United States Patent [19]

Bremer et al.

[11] Patent Number: 5,723,102
[45] Date of Patent: Mar. 3, 1998

[54] PROCESS FOR THE PREPARATION OF AN ORGAN-SPECIFIC SUBSTANCE LABELED WITH TECHNETIUM-99M

[75] Inventors: Karl-Heinz Bremer, Bad Soden am Taunus; Ludwig Kuhlmann; Alexander Schwarz, both of Flörsheim am Main; Axel Steinsträsser, Liederbach, all of Germany

[73] Assignee: CIS Bio International, Cedex, France

[21] Appl. No.: 466,259

[22] Filed: Jun. 6, 1995

Related U.S. Application Data

[63] Continuation of Ser. No. 396,897, Mar. 1, 1995, which is a continuation of Ser. No. 257,931, Jun. 1, 1994, abandoned, which is a continuation of Ser. No. 126,018, Sep. 23, 1993, abandoned, which is a continuation of Ser. No. 907,746, Jun. 29, 1992, abandoned, which is a division of Ser. No. 680,114, Apr. 3, 1991, Pat. No. 5,164,175, which is a division of Ser. No. 427,990, Oct. 27, 1989, Pat. No. 5,116,596, which is a continuation of Ser. No. 130,183, Dec. 8, 1987, abandoned.

[30] Foreign Application Priority Data

Dec. 10, 1986 [DE] Germany .................. 36 42 173.1
Aug. 27, 1987 [DE] Germany .................. 37 28 599.8

[51] Int. Cl.$^6$ .................. A61K 51/00; A61M 36/14
[52] U.S. Cl. .................. 424/1.69; 424/1.49; 424/1.11; 206/569
[58] Field of Search .................. 424/1.69, 1.11, 424/1.37, 1.49, 1.45; 206/569, 223, 570; 530/387.1, 387.2, 388.1; 436/512, 547, 548

[56] References Cited

U.S. PATENT DOCUMENTS

| | | |
|---|---|---|
| 3,987,157 | 10/1976 | Molinski et al. .................. 424/1.11 |
| 4,057,615 | 11/1977 | Bardy et al. .................. 424/1 |
| 4,272,503 | 6/1981 | Camin et al. .................. 424/1.11 |
| 4,337,240 | 6/1982 | Saklad .................. 424/1.11 |
| 5,053,493 | 10/1991 | Pak et al. .................. 530/402 |
| 5,061,641 | 10/1991 | Shochat et al. .................. 436/545 |
| 5,102,990 | 4/1992 | Rhodes .................. 530/391.5 |

FOREIGN PATENT DOCUMENTS

| | | |
|---|---|---|
| 0 035 265 B1 | 9/1981 | European Pat. Off. . |
| 0 111 414 A2 | 6/1984 | European Pat. Off. . |
| 0 179 481 A3 | 4/1986 | European Pat. Off. . |
| WO 85/03063 | 7/1985 | WIPO . |

OTHER PUBLICATIONS

A. Bardy et al., Technetium–99m Labeling by Means of Stannous Pyrophosphate, J. Nucl. Med., 16(5):435–437 (1975).

A. Khentigan et al., Effects of Prior Administration of Sn(11) Complexes on In Vivo Distribution of 99m-Tc-Pertechnetate, J. Nucl. Med., 17(5): 380–384 (1975).

B.A. Rhodes et al., 99mTc–Labeling and Acceptance Testing of Radiolabeled Antibodies and Antibody Fragments, Tumor Imaging 111–123 (1982).

William A. Pettit et al., Radiolabeling of Affinity–Purified Goat Anti–Carcinoembryonic Antigen Immunoglobulin G with Technetium–99m, Cancer Research, 40:3043–3045 (1980).

*Primary Examiner*—John Kight
*Assistant Examiner*—Dameron Jones
*Attorney, Agent, or Firm*—Finnegan, Henderson, Farabow, Garrett & Dunner, L.L.P.

[57] ABSTRACT

The invention relates to a process for the preparation of an organ-specific substance labeled with technetium-99m, in which an organ-specific substance, or an organ-specific substance which has been pretreated or coupled to a complexing agent for technetium-99m, is mixed with [99m]-pertechnetate and a complex-stabilized reducing agent.

12 Claims, No Drawings

PROCESS FOR THE PREPARATION OF AN ORGAN-SPECIFIC SUBSTANCE LABELED WITH TECHNETIUM-99M

This is a Rule 60 continuation of application Ser. No. 08/396,897 filed Mar. 1, 1995, which is a continuation of 08/257,931, filed Jun. 1, 1994, abandoned, which is a continuation of application Ser. No. 08/126,018 filed Sep. 23, 1993, now abandoned, which is a continuation of application Ser. No. 07/907,746 filed Jun. 29, 1992, abandoned, which is a divisional of application Ser. No. 07/680,114 filed Apr. 3, 1991, U.S. Pat. No. 5,164,175, which is a divisional of application Ser. No. 07/427,990 filed Oct. 27, 1989, U.S. Pat. No. 5,116,596, which is a continuation of application Ser. No. 07/130,183 filed Dec. 8, 1987, abandoned.

SPECIFICATION

The invention relates to a process for the preparation of an organ-specific substance labeled with technetium-99 m, to a test kit suitable for its preparation, and to a diagnostic aid containing the labeled organ-specific substance.

Since the pioneering work of Milstein and Köhler, who in 1975 published a process in which antibody-secreting mouse B lymphocytes are fused with mouse myeloma cells, and the product of fusion of the two cells, the hybrid, continues to grow and produces antibodies, it has been possible to isolate from the large number of resultant hybrids the one which produces an antibody of defined specificity. These monoclonal antibodies, which recognize only one defined epitope on the corresponding antigen, are now available in relatively large amounts for immunoscintigraphy. Monoclonal antibodies against tumor-associated antigens are suitable for methods of tumor localization and for detecting recurrences and metastases. For this purpose, it is necessary for the antibody to be radiolabeled before the injection, in order to establish, using suitable nuclear medical diagnostic imaging techniques, whether there is a tumor carrying the antigen in the body. Of the radionuclides which are most frequently used nowadays in nuclear medical diagnostic methods, iodine isotopes are most straightforward to use for labeling proteins. In this connection, iodine-123 most nearly meets practical requirements, such as satisfactory detection efficiency and low radiation exposure, because it is a pure γ emitter and has a favorable γ energy of 159 keV. Its relatively short half-life of 13.2 hours and, in particular, the fact that its production is tied to particle accelerators, which is also the reason for its relatively high price, greatly restrict the use of iodine-123 for antibody labeling.

Iodine-131, which is not an ideal radionuclide for in vivo diagnostic methods because the energy of its γ radiation is unfavorable for γ cameras and because its β emission is undesired from the viewpoint of radiation exposure, is widely used for antibody labelings because $^{131}I$ can be obtained at reasonable cost with high activity concentration and with sufficiently high specific activity, and hence relatively straightforward and low-cost labeling is possible.

The crucial disadvantage of all iodine-labeled antibodies is that, in vivo, the radioactive iodine is partially eliminated from the antibody by deiodination processes and is then present in the body as iodide which, on the one hand, accumulates in the thyroid and, on the other hand, increases the background activity because iodide is eliminated relatively slowly from the blood. In every case when iodine-labeled antibodies are administered it is necessary for there to have been previous blocking of the thyroid of the person who is to be investigated. A certain advantage of iodine-labeled antibodies which emerges is that their accumulation in the liver and kidneys at the customary time of investigation is distinctly lower than with the same antibodies labeled with other radionuclides.

Recently, $^{111}In$ has been widely used for antibody labelings. Since it is a metallic element, in contrast to iodine, indium cannot be directly bound to proteins. It is necessary for this purpose to have bifunctional chelating agents which are able, on the one hand, to undergo covalent bonding with the protein and, on the other hand, to bind to the antibody, via a strong complexing group, the indium which is in the form of a cation.

The Komplexon which is used most often for this purpose is diethylenetriaminepentaacetic acid (DTPA). DTPA is reacted as bicyclic anhydride with the antibody. During this, it initially undergoes covalent amide bonding to terminal amino groups of the protein, while its remaining acid group is subsequently liberated by reaction with water. The antibody which has been derivatized in this way is now able to bind firmly the radionuclide, which is added as $^{111}In$ citrate. The indium must be offered as a labile complex compound, since otherwise it would precipitate out at the required pH values. The bicyclic anhydride of DTPA is not an ideal reagent because it may undergo inter- and intramolecular coupling reactions via its bifunctionality.

Whereas gallium has no advantages over indium, the technetium-99 m labeling of potential diagnostic aids is aspired after, since $^{99m}Tc$ has become the most important radionuclide in nuclear medical diagnostic methods because of its favorable physical properties (absence of particle emission, γ energy of 140 kev and half-life of 6 hours) and the low radiation exposure associated therewith.

Technetium-99 m can be obtained from nuclide generators and is initially in the form of the pertechnetate, which is suitable for thyroid and brain scintigraphy, for example. Scintigraphy of other organs using technetium-99 m is possible with the aid of certain "transport substances", which, on the one hand, are able to bind technetium and, on the other hand, concentrate the radionuclide in the target organ with high selectivity. The substances which have hitherto been mainly used for this purpose can be directly labeled with technetium- 99 m and have high organ specificity. However, there is, in addition, a number of substances which, although having high organ specificity, cannot be directly labeled. These may be proteins (fibrinogen, human serum albumin), enzymes (streptokinase, lactate dehydrogenase), sugars (dextran, glucose) or polymers. They also include low molecular weight substances, such as fatty acids, which concentrate in myocardial tissue owing to the high energy requirements of the heart.

In order to label the organ-specific "transport substance" with technetium-99 m it is necessary for the pertechnetate which is eluted from the nuclide generator first to be converted into a lower oxidation state. In this reduced form, technetium forms more or less stable compounds with the organ-specific substance. For bone scintigraphy, for example, $^{99m}Tc$/phosphorus acid derivatives, especially organic phosphonic acids, are used. Thus, the organ-specific "transport substance" in the labeling unit described in European Patent 2485 is the sodium salt of, 3-diphosphono-1,2-propanedicarboxylic acid. $^{99m}Tc$/tri- and tetraphosphonic acids are described in European Patent 108.253for the scintigraphic visualization of the RES, in particular of the liver. The $^{99m}Tc$ complex with diethylenetriaminepentaacetic acid (DTPA) is used in methods of diagnosing kidney diseases and pathological processes in the brain.

Since direct labeling of, for example, antibodies with technetium is impossible, attempts have been made, in a manner similar to indium labeling, to like use of bifunctional complexing agents to achieve stable technetium labeling of antibodies. The particular problem in labeling with technetium is that tin(II) ions are normally present in the reaction solution. To date tin(II) has been the only reducing agent which makes it possible at room temperature to convert the pertechnetate rapidly and quantitatively into a lower, and thus reactive, oxidation state. The tin(II) and (IV) ions which are present in addition to the reduced technetium compete for the binding sites on the complex which is coupled to the antibody, so that either the complexing agent must be used in excess, which may effect the specific properties of the antibody, or unbound technetium and tin as a conjoint colloid results in undesired radioactivity accumulation in other organs.

U.S. Pat. No. 4,479,930 states that the cyclic anhydrides of DTPA and EDTA are chelating agents not only for $^{111}$In and $^{67}$Ga but also for $^{99m}$Tc. European Patent 33,765 mentions the use of deferoxamine as an agent for complexing technetium-99 m to proteins. In International Patent Application WO 85/3063, the partially reduced disulfide bridges in the antibody are reacted with the sodium salt of tetrachloronitridotechnetate, which must previously be prepared by reaction of pertechnetate with sodium azide. In European Patent Application 194,853, use is likewise made of free thiol groups, generated by reduction in antibody fragments, for the binding of a chelating complex which is [(7-maleimidoheptyl)imino-bis(ethylenenitrilo)]-tetraacetic acid, which has a rather elaborate synthesis. The complex is coupled to the antibody by reaction of the SH groups with the double bond in the maleimide part of the complex compound, while the radioactive metal ion is complexed by the nitrilodiacetic acid residues.

More straightforward methods for the $^{99m}$Tc labeling of antibodies and antibody fragments are described in European Patent 5638 and U.S. Pat. No. 4,478,815. In these, tin(II) salts are used in excess for the simultaneous reductive cleavage of disulfide bridges and reduction of the added $^{99m}$Tc-pertechnetate. In general, relatively long incubation times (24 h) are required for cleavage of the —S—S— bond, during which F(ab')$_2$ fragments are partially cleaved to F(ab') fragments. Recent statements in the literature (for example Journal Nuclear Medicine 27 (1986), pages 685–93 and 1315–20, and International Journal of Nuclear Medicine Biology 12 (1985) pages 3–8) show that the ratio of the two fragments depends on the "tinning reaction" and that the ratio of the two components does not change to any noteworthy extent after the $^{99m}$Tc labeling, the main component being $^{99m}$Tc-labeled F(ab'). It was necessary in every case subsequently to purify the labeled F(ab') fragment, because quantitative conversion of the pertechnetate was not achieved despite a reaction time of at least 30 minutes.

It has not hitherto been possible to use the labeling processes described above to prepare products which can be used routinely without elaborate processing steps.

A process for the preparation of an organ-specific substance labeled with technetium-99 m has now been found, in which an organ-specific substance, or an organ-specific substance which has been pretreated or coupled to a complexing agent for technetium-99 m, is mixed with [99 m]-pertechnetate and a complex-stabilized reducing agent.

It is possible in this way to label with technetium-99 m those organ-specific substances ("carrier substances") which have in their molecule at least one functional group having complexing properties. Groups of this type usually take the form of atoms or ions having an electron-paired donor function (Lewis bases). A functional group of this type having complexing properties is, for example, a —SCN, —NH$_2$, —NHR, —NR$_2$, —COO—, —ON, =S, —H or —NO group.

Representative examples which may be mentioned of substances of this type having functional complexing groups are: proteins (—NH—, —NH$_2$ or _COO—groups), enzymes (—NH$_2$, —OH and —P=O groups), sugars (—OH groups) or polymers which have side chains having appropriate functional groups.

If the compound which is to be labeled does not have a functional group of this type, the substance must, before labeling, be "pretreated" or coupled to a suitable complexing agent.

By "pretreated" in the sense of the invention there are meant those measures which result in the generation of a functional group having complexing properties in the molecule which is to be labeled. For example, antibodies contain disulfide bridges. However, the two sulfur atoms which are covalently linked together are not, in this form, able to complex technetium-99 m. If, however, the disulfide bridge is reduced, there are generated two SH groups which, in turn, now represent excellent complexing ligands for technetium-99 m and, moreover, bind the latter in good yields.

Another possibility of binding technetium-99 m to organ-specific substances which do not have a functional group having complexing properties comprises incorporation of a functional group of this type into the molecule, or chemical bonding of a complexing agent onto the molecule.

An essential point of the invention is that the substance which is to be labeled does not come into direct contact with the reducing agent—preferably tin(II) salt. In the first place, the tin(II) salt is separately mixed with a suitable reactant, there being formation of a complex-stabilized reducing agent. The reactant may be a phosphorus compound such as, for example, a phosphonate or a pyrophosphate, a generally good complexing agent such as, for example, ethylenediaminetetraacetic acid, or another reagent which reacts with tin(II) in such a way that it keeps the tin(II) in solution at a physiological pH (6–8) and thus maintains the reducing agent in a state capable of functioning (complex-stabilized reducing agent).

The process appears to be particularly interesting for the technetium-99 m labeling of antibodies. Partial reduction of the S—S bonds of the antibody or of a F(ab')$_2$ antibody fragment can be achieved at room temperature by the brief action of mild reducing agents (pretreatment of the organ-specific substance). Particularly suitable reducing agents are monothiols such as 2-mercaptoethanol, or 2-mercaptoethylamine (cysteamine). This results in reactive antibody molecules which have neither suffered a loss of immunological reactivity nor been fragmented into smaller pieces. In principle, reducing agents suitable for the partial reduction of the antibody or of the F(ab')$_2$ antibody fragment are all those which, even when they act for a longish time, cleave only some of the S—S bonds and result in no fragmentation of the antibody component. The time for which a reducing agent of this type acts on the antibody component need not exceed one hour. In general, a sufficient number of SH groups has been produced after only 10 to 30 minutes for adequate amounts of technetium-99 m cations to be bound. The excess reducing agent is then removed, and the partially reduced antibody is isolated in a buffered solution (for example 0.02M phosphate solution, pH 7.2) and freeze-dried without delay. During this, it is necessary to suppress reoxidation of the free thiol groups in the antibody by atmospheric oxygen. The freeze-dried antibody, which contains no additives apart from the buffer salts and is blanketed with nitrogen as protective gas, can be kept at refrigerated temperature (−5° to +5° C.) for some weeks without change; it dissolves again satisfactorily on addition of isotonic saline.

The partially reduced antibody component prepared in this way (pretreated organ-specific substance) can now be smoothly labeled with technetium-99 m by addition of a mixture of pertechnetate and tin(II) phosphonate or pyrophosphate. It is particularly advantageous to use diphosphonates, triphosphonates or tetraphosphonates as tin(II) phosphonates. The tin(II) salts of methanediphosphonic acid, of aminomethanediphosphonic acid, of 3,3-diphosphonopropionic acid, of 3,3-diphosphono-1, 2-propanedicarboxylic acid or of propane-1,1,3,3-tetraphosphonic acid have proved to be very particularly suitable.

These tin-containing phosphonate complexes have already been described in European Patents 2,485 and 108,253, and they are widely used as a technetium labeling kit for scintigraphy of the skeleton and liver. Tin(II)-containing pyrophosphate is equally suitable, whereas the tin(II) salt of diethylenetriaminepentaacetic acid is unsuitable.

The procedure for the preparation of a diagnostic aid ready for use can be such that initially the freeze-dried antibody component is dissolved in a technetium-99 m pertechnetate solution, and then the reduction and binding of the technetium to the antibody is brought about by addition of a solution of the tin(II) component.

However, it is also possible to prepare the diagnostic aid by initially dissolving the antibody component in the tin(II) -containing solution, and then labeling the antibody with technetium by addition of technetium-99 m-pertechnetate solution.

It is expedient, for the preparation of a diagnostic aid which contains a technetium-99 m-labeled organ-specific substance, to make up a test kit which contains two separate, preferably freeze-dried, components, one of which contains the organ-specific substance or the pretreated organ-specific substance, or the organ-specific substance which has been coupled to a complexing agent for $^{99m}$Tc, where appropriate mixed with a buffer, and the other contains the complex-stabilized reducing agent, preferably the complex-stabilized tin(II) salt, which is required for the reduction and binding of the technetium to the organ-specific substance. A particularly suitable test kit has proved to be one in which the freeze-dried, where appropriate pretreated, organ-specific substance is mixed with disodium hydrogen phosphate (pH 7.2) as buffer substance. In this way, after a short reaction time, for example after only 5 minutes, there is virtually quantitative technetium-99 m labeling of the substance, which contains less than 1% free pertechnetate and only very small amounts of the $^{99m}$Tc-labeled tin(II) component as impurities, so that subsequent purification processes are no longer necessary.

Having the organ-specific substance and the tin(II) component in separate containers ensures that the freeze-dried product can be stored unchanged. This ensures rapid and satisfactory labeling of the organ-specific substance without difficulty. The amount of tin(II) required for the reduction of the pertechnetate is, of course, small, of the order of a few micrograms. In each case, 1 to 100 micrograms, preferably 5 to 10 micrograms, based on tin(II), of the tin-containing phosphonate or pyrophosphate is added for each 1 mg of the organ-specific component in order to achieve stable labeling with technetium-99 m.

The tin(II) phosphonates or pyrophosphates to be used according to the invention are particularly suitable for the labeling of reduced antibodies or reduced antibody fragments because, at the neutral pH necessary for labeling, they form a stable complex which, however, only loosely binds the reduced technetium cation so that it can easily be exchanged with the thiol groups in the antibody or its fragment.

The stabilizer which is present in some labeling kits is also advantageous in antibody labeling because it guarantees that the injection solution can be stored for a lengthy period. Excellent stability of the technetium-99 m-labeled antibodies can be achieved by N-(4-amino-benzoyl) glutamic acid which is described in European Patent Application 141,100 and can be used as stabilizing component in the diphosphonates employed for skeletal scintigraphy.

The technetium-99 m-labeled antibody or its F(ab')$_2$ antibody fragment prepared according to the invention are preferably used for the in vivo detection of tumors. Preferably used is a monoclonal antibody or its F(ab')$_2$ fragments which react with tumor-associated antigens.

EXAMPLE 1

20 mg of the monoclonal antibody BW 431/31 which is directed against carcinoembryonic antigen (CEA) and is used for the diagnosis of colorectal carcinomas were dialyzed at room temperature to remove additives, such as sucrose, and to transfer it into isotonic saline. This antibody is described in German Offenlegungsschrift 3,416,774 and by Bosslet et al., Int. J. of Cancer 36, 75–84 (1985).

The antibody was then present in a concentration of about 5 mg per ml and was reacted with a total of 20 mg of 2-mercaptoethanol at room temperature (30 minutes), and then excess reducing agent was removed by gel filtration on BioGel P-2, a polyacrylamide gel from BioRad. The antibody dissolved in 0.02M phosphate buffer (pH 7.2) was isolated and freeze-dried without delay. Each of the containers of freeze-dried sample contained 2 mg of the antibody and about 1.4 mg of disodium hydrogen phosphate.

For the technetium-99 m labeling, the samples were each reacted with 7.5 ml of pertechnetate solution containing a total of up to 3,000 MBq (about 80 mCi. The tin(II) component used was a freeze-dried labeling unit composed of 5 mg of the sodium salt of 3,3-diphosphonopropionic acid, 0.1 mg of tin(II) cations and 0.5 mg of N-(4-amino-benzoyl)-L-glutamic acid. This mixture was dissolved in 5 ml of physiological saline and, immediately thereafter (after one minute), 0.5 ml of this solution was added to the antibody solution, so that the total volume was 8 ml. After a reaction time of 10 minutes, the labeling yield was checked by thin-layer chromatography, gel filtration on BioGel P-10 and high-pressure liquid chromatography on Zorbax GF 250 from DuPont.

More than 95% of the technetium-99 m activity was protein-bound, about 1% was present as fractions bound to phosphonate, while less than 1% was pertechnetate. The proportion of pertechnetate rose only on standing for a lengthy period; it was about 2% after 6 hours, while the fraction bound to phosphonate remained at 1%.

Determination of the fraction with immunoreactivity in various technetium-99 m-labeled antibodies by measurement of the binding to tumor cells produced values for the immunoreactivity which agreed well with corresponding CEA antibodies labeled with iodine-131 and indium-111 (Table 1).

TABLE 1

Comparison of the immunoreactivity (%) of monoclonal antibodies labeled with the radionuclides $^{131}$I, $^{111}$In and $^{99m}$Tc.

| Monoclonal antibody | $^{131}$I | $^{111}$In | $^{99m}$Tc |
|---|---|---|---|
| BW 431/31 | 85 | 75 | 90 |
| BW 431/26 | 85 | 70 | 95 |
| BW 494/32 | 65 | 45 | 70 |

The monoclonal antibody BW 431/26 mentioned in the table is disclosed in German Offenlegungsschrift 3,416,774 and is called MAb VIII there. The monoclonal antibody BW 4941/32 is described in German Patent Application P 35 31 301.3.

EXAMPLE 2 (Comparison Example)

The monoclonal antibody BW 431/31 was treated in the same manner as in Example 1, but was not reacted with 2-mercaptoethanol. The antibody thus contained no free thiol groups, and the product of reaction with pertechnetate in the presence of an equal amount of tin diphosphonate, carried out as in Example 1, had only about 1% of the technetium-99 m protein bound, while the major proportion (more than 50%) was in the form of technetium-99 m diphosphonate, and a considerable proportion of free pertechnetate (15%) was still present in addition to reduced, unbound technetium (31%).

EXAMPLE 3

For the technetium-99 m labeling of the monoclonal antibody BW 494/32, which is directed against a pancreatic carcinoma-associated mucus antigen, 20 mg of this substance was dissolved in 2 ml of isotonic saline, 0.5 ml of a 1% strength aqueous solution of cysteamine hydrochloride was added, and the mixture was incubated at room temperature for 20 minutes. The modified antibody which had been purified by column chromatography was dissolved in 0.02M Na$_2$HPO$_4$ buffer solution and freeze-dried in 2 mg portions. The tin(II) component used for the technetium labeling of the antibody was a pyrophosphate labeling kit which contains 7.2 mg of Na$_4$P$_2$O$_7$ and 1.03 mg of tin(II) chloride per kit. The contents in one container was dissolved in 10 ml of physiological saline, and 0.25 ml, corresponding to about 14 μg of Sn$^{2+}$, of this solution was added to the antibody which had previously been dissolved in about 8 ml of pertechnetate solution (about 2,000 MBq). After a reaction time of 10 minutes, 0.1 ml portions of the solution, having the following composition 25 μg of MAb
2.25 μg of Na$_4$P$_2$O$_7$
0.175 μg of tin(II) and about
18 μg of Na$_2$HPO$_4$ buffer were administered i.v. to healthy rats. The organ distribution 24 hours after injection (p.i.) is shown in Table 2. It is evident from this that the accumulation in bone, thyroid and stomach is very low, and in the other organs is comparable to the iodine-131-labeled antibody. The measured immunoreactivity (cf. Table 1) for the technetium-99 m-labeled antibody BW 494/32 was higher than on labeling with iodine-131 or indium-111.

TABLE 2

Organ distribution of $^{99m}$Tc- and $^{131}$I-MAb 494/32 in normal Wistar rats 24 h p.i. (as % of the administered dose per organ or per gram of tissue).

| Organ | $^{99m}$Tc | $^{131}$I |
|---|---|---|
| Liver %/g | 0.49 | 0.23 |
| Lungs | 0.82 | 0.48 |
| Spleen | 0.65 | 0.30 |
| Kidneys | 4.25 | 0.70 |
| Bone | 0.57 | 0.20 |
| Blood | 1.97 | 0.92 |
| Muscle | 0.12 | 0.08 |
| Stomach % total | 0.38 | 2.50 |
| Thyroid | 0.05 | 4.85 |
| Intestine | 3.83 | 4.62 |
| Urine | 24.5 | 49.3 |

EXAMPLE 4

50 mg of the monoclonal antibody BW 431/26, which likewise directed against CEA, were partially reduced by treatment with 2-mercaptoethanol, and the product was purified and freeze-dried in 2 mg portions in the presence of phosphate buffer (p H 7.2).

The $^{99m}$Tc labeling was carried out using a labeling unit which is otherwise used for liver scintigraphy and is composed of 13.5 mg of tetrasodium 1,1,3,3-propanetetraphosphonate and 0.6 mg of tin(II) chloride× 2H$_2$O. The contents of a labeling unit were dissolved in 10 ml of isotonic saline, and 0.5 ml of this, corresponding to 15 μg of Sn$^{2+}$, were added to the freeze-dried antibody. Pertechnetate solution (3,000 MBq) was then added to the clear antibody/Sn(II) salt solution, and $^{99m}$Tc-labeled antibody was administered i.v. to nude mice having a human colon carcinoma implants. The tumor was readily visualized by scintigraphy as early as 26 hours p.i. Table 3 shows, on the basis of the tumor accumulation and organ distribution of this antibody in the nude mouse, that the products labeled with $^{131}$I, $^{111}$In and $^{99m}$Tc are comparable.

TABLE 3

Tumor accumulation and organ distribution of $^{131}$I-, $^{111}$In- and $^{99m}$Tc-MAb 431/26 in nude mice (n = 2) with human colon carcinoma as a function of time

| After injection | $^{131}$I | | $^{111}$In | | $^{99m}$Tc | |
|---|---|---|---|---|---|---|
| (p.i.) (h) | 17 | 48 | 17 | 48 | 17 | 30 |
| Tumor %/g | 14.9 | 8.8 | 9.8 | 13.0 | 11.0 | 14.9 |
| Liver %/g | 4.6 | 3.0 | 8.5 | 8.4 | 7.2 | 5.4 |
| Kidneys %/g | 3.4 | 1.9 | 12.2 | 16.4 | 10.6 | 7.7 |
| Muscle %/g | 1.3 | 0.84 | 1.4 | 1.2 | 0.9 | 1.0 |
| Blood %/ml | 14.6 | 13.0 | 20.5 | 9.2 | 17.0 | 15.0 |
| Bone % total | 1.8 | 1.7 | 4.7 | 4.3 | 2.4 | 2.1 |

EXAMPLE 5

20 mg of F(ab')$_2$ fragment of monoclonal antibody 431/31 were incubated with 1 ml of a 1% strength solution of cysteamine hydrochloride at 4° C. for 15 minutes. The excess reducing agent was removed from the antibody fragment, which was then freeze-dried together with phosphate buffer. For labeling with technetium, use was made of a labeling unit composed of 13.0 mg of tetrasodium 3,3-diphosphono-1,2-propanedicarboxylate, 0.23 mg of tin(II) oxide and 1.0 mg of monosodium N-(4-aminobenzoyl)-L-glutamate, of which 1/20 in 0.5 ml of physiological saline was used. The antibody fragment which had been labeled with a specific activity of 1,000 MBq/mg contained virtually no pertechnetate but a slightly higher proportion (about 3%) of $^{99m}$Tc diphosphonate. The immunoreactivity was 60%.

EXAMPLE 6

$^{99m}$Tc labeling of a protein 250 mg of IgG were dissolved in a concentration of 10 mg/ml in isotonic saline. 0.5 –1 ml of 2-mercaptoethanol was added to this solution, which was then incubated at 4°–25° C. for about 30 minutes. The reduced immunoglobulin was subsequently purified by gel filtration through a polyacrylamide gel column (BioGel P-2 from BioRad), eluting with 0.02 M disodium hydrogen phosphate solution (pH 7.2). The pure IgG fraction which was removed was adjusted by dilution with the same phosphate buffer to a concentration of 4 mg of IgG/ml (about 3 mg of $Na_2HPO_4$/ml), and 0.5 ml portions of this solution were placed in containers and freeze-dried.

For the $^{99m}$Tc labeling of a sample (2 mg of IgG), the lyophilisate was dissolved in 1 ml of a tin(II) methane-diphosphonate solution (pH 7) which was obtained by dissolving a labeling unit composed of 2.6 mg of sodium methanediphosphonate and 0.04 mg of tin(II) chloride in 5 ml of isotonic saline. 4–9 ml of $^{99m}$Tc-pertechnetate solution were subsequently added (about 1,000 MBq). In the $^{99m}$Tc-labeled IgG obtained after a reaction time of 5 minutes more than 95% of the technetium was protein-bound, while less than 1% of phosphonate-bound fraction and less than 1% of free pertechnetate were present. The labeled IgG was stable for up to 3 hours after preparation. Free pertechnetate was detectable again in the solution only after it had stood for lengthy periods.

EXAMPLE 7

$^{99m}$Tc labeling of 1,4,8,11-tetraazacyclotetradecane (cyclam)

8 mg of cyclam were dissolved in 0.5 ml of isotonic saline, and the pH was adjusted to 11 with 0.1N sodium hydroxide solution. To this solution was added 1 ml of a tin(II) 1,1,3,3-propanetetraphosphonate solution (pH=6) which was obtained by dissolving a labeling unit composed of 2.9 mg of sodium 1,1,3,3-propanetetraphosphonic acid sodium salt and 0.12 mg of tin(II) chloride dihydrate in 5 ml of isotonic saline. About 590 MBq of $^{99m}$Tc-pertechnetate solution (about 0.3 ml) were subsequently added, and the mixture was left to stand at room temperature for 5 min. The yield of labeled cyclam was greater than 98%, less than 1% being in the form of free pertechnetate or phosphonate-bound technetium. The labeled solution could be kept for several hours.

EXAMPLE 8

$^{99m}$Tc-labeling of pyrophosphate 10 mg of pyrophosphate were dissolved in 1 ml of 0.9% saline, and 1 ml of tin(II) 1,1,3,3-propanetetraphosphonate solution (see Example 7) was added. 1 ml of pertechnetate solution (~300 MBq) was added to the solution, and the mixture was left to stand at room temperature for 5 min. 50% of the pyrophosphate was labeled with $^{99m}$Tc. The proportion of labeled phosphonate was below 10%.

We claim:

1. A process for the preparation of an organ-specific substance labeled with technetium-99 m, which comprises mixing an organ-specific substance, or an organ-specific substance that has been pretreated or coupled to a complexing agent for technetium-99 m, with (99 m)-pertechnetate and a complex-stabilized reducing agent; wherein the reducing agent is at least one tin(II) salt of methanediphosphonic acid, aminomethanediphosphonic acid, 3,3-diphosphonopropionic acid, 3,3-diphosphono-1,2-propanedicarboxylic acid or propane-1,1,3,3-tetraphosphonic acid.

2. The process as claimed in claim 1, wherein said organ-specific substance is an antibody, a F(ab')$_2$ antibody fragment, a protein, an enzyme, a sugar, or a polymer which is suitable for diagnostic purposes.

3. The process as claimed in claim 2, wherein said antibody is a monoclonal antibody or its F(ab')$_2$ fragment.

4. The process as claimed in claim 3, wherein said monoclonal antibody or its F(ab')$_2$ fragment is directed against tumor-associated antigens.

5. A test kit comprising two separate freeze-dried components, one of which contains an organ-specific substance, and the other which contains a complex-stabilized reducing agent that is required for the reduction and binding of technetium-99 m to the organ-specific substance, wherein the organ-specific substance is a partially reduced antibody or its F(ab')$_2$ fragment and the reducing agent is at least one tin(II) salt of methanediphosphonic acid, aminomethanediphosphonic acid, 3,3-diphosphonopropionic acid, 3,3-diphosphono-1,2-propanedicarboxylic acid or propane-1,1,3,3-tetraphosphonic acid.

6. A test kit as claimed in claim 5, wherein the freeze-dried antibody component is mixed with disodium hydrogen phosphate as buffer substance.

7. A diagnostic aid whose preparation entails initially dissolving a component which contains an organ-specific substance in a technetium-99 m-pertechnetate solution, and bringing about the reduction and binding of the technetium to the organ-specific substance by addition of a complex-stabilized reducing agent; wherein the reducing agent is at least one tin(II) salt of methanediphosphonic acid, aminomethanediphosphonic acid, 3,3-diphosphonopropionic acid, 3,3-diphosphono-1,2-propanedicarboxylic acid, or propane-1,1,3,3-tetraphosphonic acid.

8. A diagnostic aid whose preparation entails initially dissolving a component which contains an organ-specific substance in a solution of a complex-stabilized reducing agent; wherein the reducing agent is at least one tin(II) salt of methanediphosphonic acid, aminomethanediphosphonic acid, 3,3-diphosphonopropionic acid, 3,3-diphosphono-1,2-propanedicarboxylic acid or propane-1,1,3,3-tetraphosphonic acid, and then labeling the organ-specific substance with technetium-99 m by addition of a technetium-99 m-pertechnetate solution.

9. A diagnostic aid as claimed in claim 7, wherein the complex-stabilized reducing agent is at least one tin(II) salt of methanediphosphonic acid, aminomethanediphosphonic acid, 3,3-diphosphonopropionic acid, 3,3-diphosphono-1,2-propanedicarboxylic acid or propane-1,1,3,3-tetraphosphonic acid, there being added in each case 1 to 100 micrograms, based on tin(II), of this reducing agent for each 1 mg of the organ-specific substance in order for the labeling of the latter with technetium-99 m to be stable.

10. A diagnostic aid as claimed in claim 8, wherein the complex-stabilized reducing agent is a tin-containing phosphonate or pyrophosphate, there being added in each case 1 to 100 micrograms, based on tin(II), of this reducing agent for each 1 mg of the organ-specific substance in order for the labeling of the latter with technetium-99 m to be stable.

11. A diagnostic aid as claimed in claim 9, wherein the complex-stabilized reducing agent being added in each case is 5 to 10 micrograms.

12. A diagnostic aid as claimed in claim 10, wherein the complex-stabilized reducing agent being added in each case is 5 to 10 micrograms.

* * * * *